US009006480B2

(12) United States Patent
Steiger et al.

(10) Patent No.: US 9,006,480 B2
(45) Date of Patent: Apr. 14, 2015

(54) PROCESS FOR PRODUCING ISOCYANATES

(75) Inventors: Wolf Steiger, Geretsried (DE); Peter Bissinger, Diessen (DE)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

(21) Appl. No.: 13/638,817

(22) PCT Filed: Apr. 4, 2011

(86) PCT No.: PCT/US2011/031061
§ 371 (c)(1),
(2), (4) Date: Oct. 1, 2012

(87) PCT Pub. No.: WO2011/130032
PCT Pub. Date: Oct. 20, 2011

(65) Prior Publication Data
US 2013/0023694 A1    Jan. 24, 2013

(30) Foreign Application Priority Data

Apr. 14, 2010 (EP) ..................... 10159888

(51) Int. Cl.
  C07C 263/00   (2006.01)
  C07C 69/52    (2006.01)
  C07C 265/00   (2006.01)
  C07C 267/00   (2006.01)
  C07C 291/00   (2006.01)
  C07C 263/08   (2006.01)

(52) U.S. Cl.
  CPC .................. C07C 263/08 (2013.01)

(58) Field of Classification Search
  CPC ........................ C07C 263/08; C07C 263/04
  USPC .......................... 560/222, 338, 330
  See application file for complete search history.

(56) References Cited

U.S. PATENT DOCUMENTS

| 2,718,516 A | 9/1955 | Bortnick |
| 2,821,544 A | 1/1958 | Holtschmidt |
| 4,176,232 A | 11/1979 | Lewis |
| 4,194,052 A | 3/1980 | Lewis |
| 4,278,809 A | 7/1981 | Burdett |
| 4,395,569 A | 7/1983 | Lewis |
| 4,916,233 A | 4/1990 | Ueno |
| 5,073,440 A | 12/1991 | Lee |
| 5,457,229 A | 10/1995 | Alper |
| 7,504,518 B2 | 3/2009 | Miyata |
| 8,124,714 B2 | 2/2012 | Bissinger |
| 2009/0258999 A1 | 10/2009 | Bissinger |

FOREIGN PATENT DOCUMENTS

| CA | 2100718 | 2/1994 |
| EP | 0408277 | 1/1991 |
| EP | 0849258 | 6/1998 |
| EP | 0936214 | 8/1999 |
| JP | H02129163 | 5/1990 |
| JP | H02-145554 A | 6/1990 |
| JP | 05058982 | 3/1993 |
| WO | WO 2005/012237 | 2/2005 |
| WO | WO 2005/092842 | 10/2005 |

OTHER PUBLICATIONS

Staab, H.A., Representation of isocyanates, Angew. Chem. 73, 66 (1961).*
Jencks et al., Imidazole Catalysis: II. Acyl transfer and the Reactions of Acetyl Imidazole with Water and Oxygen Anions, J. Biol. Chem. 234, 1272-1279 (1959).*
Matuszak et al., "Readily available anhydrous ether solutions of hydrogen chloride," J. Chem. Educ., 44(2), 108, 1967.*
Segura et al., "Chapter 3, Chemistry of Polyurethane Adhesives and Sealants," pp. 101-104, from Handbook of Adhesives and Sealants, P. Cognard (Editor), 2005.*
Extended EP Search Report for EP 10 15 9888 dated Aug. 31, 2010.
Fravel et al. 1984. Ind. Eng. Chem. Prod. Res. Dev. 23:586-590.
Houben-Weyl. 1983. Methoden Der Organischen Chemie. Band E4. Georg Thieme Verlag Stuttgart: New York. p. 756.
International Search Report for PCT/US11/31061 mailed Jun. 13, 2011.
Speight. 2005. Lange's Handbook of Chemistry. $16^{th}$ Ed. McGraw-Hill. Table Section 1.69:p. 1.330. "Dissociation Constants of Inorganic Acids."
Speight. 2005. Lange's Handbook of Chemistry. $16^{th}$ Ed. McGraw-Hill. Table Section 2.59:pp. 2620-2669. "$pK_a$ Values of Organic Materials in Water."
Staab. 1957. Liebigs Ann. 609:75ff.
Staab. 1961. Angew. Chem. 73:66. Representation of isocyanates.
Staab. 1962. Angewandte Chemie. International Edition. 1(7):351-367. XP 000197451. "Syntheses Using Heterocyclic Ammides (Azolides)."
Staab. 1998. Wiley-VCH. [ISBN: 3-527-29314-0]. "Azolides in organic synthesis and biochemistry." (Book—cover and Index only).

* cited by examiner

Primary Examiner — Paul A Zucker
Assistant Examiner — Mark Luderer
(74) Attorney, Agent, or Firm — 3M Innovative Properties Company; Qiang Han

(57) ABSTRACT

The invention relates a process for producing isocyanates comprising the steps of a) providing an azolide and optionally a solvent, and b) adding an acid at a temperature below about 40 C. The invention also relates to the isocyanate obtainable by such a process.

12 Claims, No Drawings

PROCESS FOR PRODUCING ISOCYANATES

FIELD OF THE INVENTION

The invention relates to a process for producing isocyanates especially isocyanates with polymerizable groups. The isocyanates can be obtained by reacting a component bearing an urea azolide moiety with a strong acid at low temperature.

BACKGROUND ART

Isocyanates, especially 2-Methyl-acrylic acid 2-isocyanato-ethyl ester (MOI), are versatile organic compounds and many different routes for their production are known:
- via phosgenation of 2-(2-Methyl-acryloyloxy)-ethyl-ammonium 4-Chlorophenyl-sulfonates as described in DE 1929581,
- via phosgenation of 2-(2-Methyl-acryloyloxy)-ethyl-ammonium; chloride as described in U.S. Pat. No. 2,821,544,
- via phosgenation of isopropenyl-oxazolidin as described in EP 0 000 144,
- via phosgenation of oxazolinidone as describe in JP 1990-145555,
- via cleavage of an urethane using $PCl_5$ as described in U.S. Pat. No. 2,718,516,
- via cleavage of an urethane using chlorosilane as described in EP 0 849 258,
- via cleavage of an urethane using boron chloride as described in U.S. Pat. No. 5,457,229 or
- via dehydrohalogenation as described in WO 2005/092842.

However, most of the processes described above require the use of phosgene, which is often not desirable. Phosgene is a highly reactive gas and considered to be toxic.

Moreover, the isocyanates which are obtained by using phosgene typically contain a considerable high amount of chloride, which is often not desirable. Moreover, other undesirable contaminations like phosphorus- or silane-compounds or saturated isocyanate esters are sometimes found. These undesired contaminations are sometimes difficult to remove, too.

JP 1990-129163 relates to a process which comprises the step of reacting an imidazole derivative with carbonyl chloride, reacting the resultant compound with a monoalkanolamine, and then esterifying the resultant compound using an unsaturated carboxylic acid or its chloride or ester to give an isocyanatoalkyl ester of an unsaturated carboxylic acid. According to this process the resultant compounds typically contain a large amount of by-products, which may derive from the unsaturated group (e.g., HCl adduct of the unsaturated group). This may cause disadvantages like low reaction yield and the need for further purification.

In order to lower the content of chloride a couple of additional processes are known:
- using tertiary amines as described in WO 2005/092842,
- using amines and epoxides as described in WO 2005/012237,
- using imidazoles as described in JP 05058982,
- by distillation in presence of epoxies as described in EP 0 936 214.

The above processes, however, are sometimes complicated, require additional efforts and suffer from yield losses.

SUMMARY OF THE INVENTION

Thus, there is a need for an alternative process for the production of isocyanates, especially a process which may lead to a product having less impurities or undesired by-products, especially as regards the chloride content.

According to one aspect, the present invention relates to a process for producing isocyanates comprising the steps of
- a) providing a component with an urea azolide moiety and optionally a solvent,
- b) adding an acid at a temperature below about 40° C.,
- c) optionally heating the composition to a temperature above about 70° C. and
- d) optionally removing or isolating the isocyanate from the reaction mixture.

The invention is also directed to an isocyanate obtainable according the process described in text of the invention, the isocyanate containing less than about 1000 ppm chloride.

The inventive process provides a versatile alternative to existing processes, however, by providing a couple of advantages.

It was found that the isocyanates obtained by the inventive process contain less impurities like chlorine, if compared to isocyanates obtained by processes described in the state of the art. This can be beneficial as a certain amounts of chlorine might negatively influence a variety of subsequent reactions. Thus, a low content of chlorine can be desirable. Low content of chlorine includes e.g. amounts of less than about 1000 ppm or less than about 800 ppm or less than about 600 ppm measured when analyzing the isolated isocyanate (e.g. obtained after process step d)). Thus, the resulting isocyanate may only contain chlorine in an amount from about 1 to about 1000 ppm or from about 5 to about 800 ppm or from about 10 to about 600 ppm.

A further benefit can be seen in that, the inventive process does not require the use of phosgene, a highly reactive and toxic gas which is typically not easy to handle and typically requires a lot of technical know how, special expensive safety equipment and approval by public authorities.

It was also found that the inventive process can be conducted in comparable low expensive solvents including toluene. Thus, there is no need for using more expensive solvents like acetonitrile or ethylacetate. However, the inventive process can nevertheless be conducted in those solvents or others as well, if desired.

The inventive process does also not require the use of strong bases like triethylamine. The transformation from the imidazole-carbonyl-amino ester to the desired isocyanate can be accomplished without the use of strong bases. Those bases often do not smell good and cannot be removed easily.

Moreover, the invention provides for a process which allows the production of isocyanates in comparable high yields, without the need for isolating intermediates.

The inventive process can also be carried out at a moderate temperature. This can be beneficial as the application of high temperature may facilitate the addition of e.g. HCl to C=C-double bonds, which may be present in the product. This might also lead to elevated levels of chlorine in the final product. High temperatures can also be detrimental to the stability of some of the desired isocyanates. In the case of unsaturated isocyanates polymerization can occur at elevated temperatures (e.g. above about 200° C. or above about 160° C. or above about 120° C.).

Within the description, the following terms typically have the following meaning:

An "isocyanate group" means a group having the structure —N=C=O.

The term "azolide" relates to heterocyclic amides, ureas or urethanes in which the (or one) amide nitrogen is part of an azole ring, such as imidazole, triazole, tetrazole, benzimidazole, benzotriazole, and their substituted derivatives. A more detailed description can be found in H. A. Staab "Azolides in organic synthesis and biochemistry", Wiley-VCH, 1998 [ISBN: 3-527-29314-0]. It can be preferred if no dimeric imidazoles or imidazole derivatives are present. The ring can be substituted or unsubstituted, especially substituted with C1 to C4 alkylgroups, phenyl groups or halogen like F, Cl, Br or I.

The term "carbonyl-bisazolide" relates to ureas, where both nitrogen atoms are part of an azole ring as described in the definition of azolides. A well known example of a carbonyl-bisazolide is carbonyl diimidazole (CDI, CAS-#[530-62-1]).

A "solvent or liquid" is any solvent or liquid which is able to at least partially disperse or dissolve another component at ambient conditions (e.g. 23° C.).

The term "interfere" as used in the context of the present text relates to any influence of such a substituent on at least one of the other substituents or constituents of the composition or the reaction to form an isocyanate, or both, which is detrimental to the properties of either the urea azolide product or an isocyanate formed from the urea azolide.

The term "non-reactive" means that a substance does not undergo a chemical reaction with another substance (i.e. a reaction where chemical bonds are formed) leading to a new chemical substance at the chosen reaction conditions.

The term "detrimental" as used in the context of the present text relates to a change of properties that negatively affect the usefulness of the precursors or the cured product in their intended use.

A composition or solution is "essentially or substantially free of" a certain component within the meaning of the invention, if the composition or solution does not contain said component as an essential feature. Thus, said component is not willfully added to the composition or solution either as such or in combination with other components or ingredient of other components. Ideally the composition or solution does not contain the said component at all. However, sometimes the presence of a small amount of the said component is not avoidable e.g. due to impurities contained in the raw materials used.

"Ambient conditions" within the meaning of the invention mean the conditions which the inventive solution is usually subjected to during storage and handling. Ambient conditions may, for example, be a pressure of about 900 to about 1100 mbar, a temperature of about −10 to about 60° C. and a relative humidity of about 10 to about 100%. In the laboratory ambient conditions are adjusted to about 23° C. and about 1013 mbar.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

If not indicated otherwise, wt.-% always refers to the weight of the whole composition.

DETAILED DESCRIPTION

The inventive process is useful for producing various isocyanates from azolides, especially urea azolides.

The inventive process is in particularly useful for producing e.g. 2-Methyl-acrylic acid 2-isocyanato-ethyl ester (MOI). This substance is generally not easy to synthesise and often difficult to store in pure form. It is assumed that this is mainly caused by its tendency to polymerization.

According to one embodiment, an isocyanate which can be produced or obtained by the inventive process can be characterized by formula (1):

$$G\text{-}K\text{—}NCO \tag{1}$$

with G comprising an acyloyl moiety and
K being a $C_2$ to $C_{12}$ saturated or unsaturated linear, branched, cyclic alkylidene or aromatic residue or a combination thereof (including 1,2-ethylidene, 1,2-propylidene, 1,3-propylidene, 1,4-butylidene, 1,5-pentylidene, 1,6-hexylidene, 1,8-octylidene, 1,10-decyclidene, 1,11-undecylidene or 1,12-dodecylidene residues), wherein hydrogen might be replaced by halogen (e.g. F, Cl, Br, I). The carbon chain can be interrupted by one, two, three or four oxygen atoms. That is, ether or ester moieties can be present.

Preferred isocyanates include:
Acrylic acid 2-isocyanato-ethyl ester,
2-Methyl-acrylic acid 2-isocyanato-ethyl ester,
Acrylic acid 2-isocyanato-propyl ester,
2-Methyl-acrylic acid 2-isocyanato-propyl ester,
Acrylic acid 3-isocyanato-propyl ester,
2-Methyl-acrylic acid 3-isocyanato-propyl ester,
Acrylic acid 4-isocyanato-butyl ester,
2-Methyl-acrylic acid 4-isocyanato-butyl ester,
Acrylic acid 5-isocyanato-pentyl ester,
2-Methyl-acrylic acid 5-isocyanato-pentyl ester,
Acrylic acid 6-isocyanato-hexyl ester,
2-Methyl-acrylic acid 6-isocyanato-hexyl ester,
Acrylic acid 8-isocyanato-octyl ester,
2-Methyl-acrylic acid 8-isocyanato-octyl ester,
Acrylic acid 10-isocyanato-decyl ester,
2-Methyl-acrylic acid 10-isocyanato-decyl ester,
Acrylic acid 11-isocyanato-undecyl ester,
2-Methyl-acrylic acid 11-isocyanato-undecyl ester,
Acrylic acid 12-isocyanato-dodecyl ester,
2-Methyl-acrylic acid 12-isocyanato-dodecyl ester,
Acrylic acid 1-(2,3-diisocyanato-propyl)ester,
2-Methyl-acrylic acid 1-(2,3-diisocyanato-propyl)ester,
Acrylic acid 2-(1,3-diisocyanato-propyl)ester,
2-Methyl-acrylic acid 2-(1,3-diisocyanato-propyl)ester
Acrylic acid 1,2-(3-isocyanato-propyl)diester,
2-Methyl-acrylic acid 1,2-(3-isocyanato-propyl)diester,
Acrylic acid 1,3-(2-isocyanato-propyl)diester,
2-Methyl-acrylic acid 1,3-(2-isocyanato-propyl)diester
as well as derivatives of other acids than acrylic- or 2-methy acrylic acid with the proviso that they comprise a radically polymerizable unsaturation, mixtures and combinations thereof.

The component containing the azolide moiety (also sometimes referred to as azolide or urea azolide) can be produced by various processes as described below:

It can be preferred if an amine compound is reacted with a compound according to the general formula (2)

(2)

with A comprising an azole ring connected to the carbonyl group via an N atom
or
where an amine compound is reacted in a first step with phosgene, optionally together with a trialkylamine to scavenge HCl, and in a second step with an azole under formation of an azolide.

It can be preferred if the (urea) azolide is produced by reacting a bisazolide with an amine or its respective ammonium salt.

Generally all types of carbonyl bisazolides can be used for producing the urea azolide.

Preferred substances include 1,1'-carbonyl-diimidazol (CDI) CAS-#: [530-62-1], 1,1'-carbonyl-dibenzimidazol CAS-#: [14667-54-0], 1,1'-carbonyl-di-(1,2,4)-triazol CAS-#: [41864-22-6], 1,1'-carbonyl-bis-(2-methylimidazol) CAS-#: [13551-83-29], 1,1'-carbonyl-dibenzotriazol CAS-#: [68985-05-7]. The compounds can be used alone or as a mixture of two or more of them.

The reaction can be conducted with or without solvents.

If a solvent is used, it should be a solvent which is inert with regard to the azolide reaction. In some cases THF (tetrahydrofuran), chloroform, ethyl acetate or toluene as compatibilizers may result in an accelerated reaction of the carbonyl bisazolide with the amine. Further suitable solvents include cyclohexane, dichloromethane hexane, heptane, toluene, xylene, methy tert.-butyl ether, methy ethyl ketone, acetone, dioxane or acetonitrile or mixtures of two or more of those.

Condensation catalysts, though applicable, are not necessarily required.

The reaction temperature for producing the azolide can generally be between about 0 and about 120° C. It can be preferred, if the reaction is conducted at a temperature of between about 5 and about 70° C. or between about 10 and about 40° C. or at a temperature below the boiling point of the solvent at normal pressure (e.g. about 1025 mbar), if a solvent is used.

Using temperatures below room temperature (about 23° C.) is possible though generally unnecessary. Elevated temperatures of up to about 80° C. can facilitate and accelerate the reaction which can be advantageous especially if the process is performed without solvent.

In many cases the resulting by-product azole or azolium salt crystallizes from the dissolved or solvent free urea azolides during standing. In other cases the by-product can also be removed by distillation or sublimation. The product can be filtered or washed or purified in any other desired way. However, generally crude urea azolide can already be used for most purposes.

Reaction times can be varied. It has proven to be advantageous to let the reaction run from about 0.5 to about 50 h, or from about 1 and about 30 h, or from about 2 to about 20 h or from about 5 to about 10 h. If the urea azolide is not going to be isolated, the reaction time can basically be chosen freely until a turnover of about 80% or about 90% or about 95% or about 100% (determined via $^1$H NMR spectroscopy) is obtained.

In a process according to the invention, the molar ratio of amino groups to carbonyl-bisazolide can generally be chosen freely. However, good results have, e.g., been achieved when the molar ratio of amino groups to carbonyl-bisazolide is in the range of about 1:2 to about 1:1. As carbonyl-bisazolides tend to be expensive, a molar ratio of about 1:1 is preferred and an unnecessary excess of this reagent should be avoided.

If CDI is used as bis-azolide, typical reaction conditions for the reaction with the amine component or its corresponding ammonium salt are as follows:
a) Temperature: from about 0° C. to about 100° C. or from about 10° C. to about 70° C.
b) Solvent: toluene, ethylacetate, tetrahydrofurane, chloroform.
c) Duration: from about 5 min to about 2000 min or from about 15 min to about 1000 min.
d) Molar ratio amine to CDI: from about 1:1 to about 1:1.2 or from about 1:1 to about 1:1.1.

A combination of the reaction conditions temperature (about 10° C. to about 70° C.) and solvent (toluene) or temperature (about 10° C. to about 70° C.) and solvent (ethylacetate and/or toluene) is sometimes preferred, especially if the molar ratio amine to CDI is below about 1:1.1. Such a combination might be beneficial for increasing the overall yield.

Urea azolides can also be prepared by reacting an amine or ammonium salt with phosgene in a first step to give a chloro carbamate, which subsequently is transferred into the urea azolide by adding both an equivalent azole and a HCl scavenger.

The nature and structure of the amine is not particularly limited if the desired reaction product can be obtained.

The amine can be characterized by at least one or more of the following features:
a) The amine is a primary amine (—NH$_2$).
b) Molecular weight: about 50 to about 1000 or about 55 to about 500 or about 60 to about 300.
c) The amine can be added to any carbofunctional backbone, where the carbon atom attached to the —NH$_2$ group is preferably aliphatic.
d) Moieties which can be present include saturated and unsaturated moieties like C=C double bonds, especially activated radically polymerizable double bonds, ester moieties, amide moieties, ether moieties, tert. amine moieties and/or aromatic carbocyclic rings.
e) No presence of additional nucleophilic functional groups capable of reacting with isocyanates at room temperature faster than the NH-bond in a urea group (e.g. no OH—, NH—, SH—, COOH— moieties).
f) No presence of Si-containing moieties.
g) No presence of polymeric backbones with a statistic molecular weight distribution and a molecular weight smaller then four times the repeating unit plus endcapping residues.

The combination of features a), b), c) and d) or a) and b) or b) and d) or a), b) and d) can be sometimes preferred, especially if acrylic or methacrylic esters are used or produced during the process.

A typical chemical structure for the amine compound is:

$$G\text{-}K\text{—}NH_2 \quad (3)$$

with G comprising an acyloyl moiety (including acryloyl-, methacryloyl and crotyloyl residues) and
K being a $C_2$ to $C_{12}$ saturated or unsaturated linear, branched, cyclic alkylidene or aromatic residue or a combination thereof (including 1,2-ethylidene, 1,2-propylidene, 1,3-propylidene, 1,4-butylidene, 1,5-pentylidene, 1,6-hexylidene, 1,8-octylidene, 1,10-decyclidene, 1,11-undecylidene or 1,12-dodecylidene residues), wherein hydrogen might be replaced by halogen (e.g. F, Cl, Br, I). The carbon chain can be interrupted by one, two three or four oxygen atoms (ether bridges or ester bridges).

It can be preferred to have two or three groups G attached to K and there can also be two or three —NH$_2$ groups be attached to K.

It can also be preferred if—instead of the amine —NH$_2$ compound—a corresponding ammonium (—NH$_3^+$) salt is used. Useful counter ions of corresponding ammonium salts include halide and pseudohalides including Cl$^-$, Br$^-$, F$^-$, I$^-$, or organic counterions like toluene sulfonate (tosylate, CH$_3$—C$_6$H$_4$—SO$_3^-$), benzene sulfonate (C$_6$H$_5$SO$_3^-$, methylsulfonate (mesylate) (CH$_3$SO$_3^-$) and any other anion of an acid that does not form amides with the amine easily under the conditions applied and forms salts that are at least partially soluble in unpolar or polar aprotic organic solvents used in the process described in the text of the invention. Useful solvents include hexane, heptane, cyclohexane, toluene, xylene, methy tert.-butyl ether, ethyl acetate, chloroform, tetrahydrofurane, methy ethyl ketone, acetone, dioxane, acetonitrile, or combinations and mixtures thereof.

Particularly preferred amines or the corresponding ammonium salts are shown in formula (3):

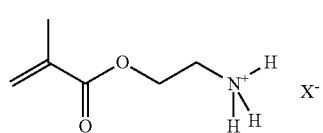

(4)

X=Cl 2-(2-Methyl-acryloyloxy)-ethyl-ammonium; chloride (MOA)
X=4-Me-$C_6H_4SO_3^-$ 2-(2-Methyl-acryloyloxy)-ethyl-ammonium; tosylate (MOTS)
X=$C_6H_5SO_3^-$ 2-(2-Methyl-acryloyloxy)-ethyl-ammonium; benzene sulfonate (MOBS)
X=$CH_3SO_3^-$ 2-(2-Methyl-acryloyloxy)-ethyl-ammonium; mesylate (MOMS)

Additional preferred compounds are the corresponding 2-acryloyloxy-ammonium salts, 2-crotoyloxy-ethyl-ammonium salts and from all these acyoxy-ethyl ammonium salts derivatives with propyl-, butyl-, pentyl-, hexyl-, octyl-, decyl, undecycl-, and dodecyl-, instead of ethyl-.

The above amine according to formula (3) or (4) can be produced by reacting a suitable amino alcohol with the respective acyloyl moiety containing reagent (e.g. (meth)acryl acid or (meth)acryl acid chloride).

Suitable amino alcohols include 2-amino-ethanol, 1-amino-2-propanol, 2-amino-1-propanole, 1-amino-3-propanol, 2-amino-1-butanole, 3-amino-1-butanol, 3-amino-2-butanole, 1-amino-2-butanole, 1-amino-3-butanole, 1-amino-2-methyl-1-propanol, 1-amino-2-methyl-2-propanol, 2-amino-2-methyl-1-propanol, 1-amino-5-pentanol, 1-amino-2-methyl-4-butanol, 1-amino-3-methyl-4-butanol, 2-amino-5-pentanol, 1-amino-4-pentanol, 1-amino-3-propanol, 3-amino-1-propanol, 1-amino-2-ethyl-3-propanol, 2-amino-4-pentanol, 1-amino-2-methyl-3-butanol, 2-amino-3-methyl-4-butanol, 1-amino-3-methyl-3-butanol, 2-amino-2-methyl-4-butanol, 1-amino-2-pentanol, 2-amino-1-pentanol, 1-amino-3-methyl-2-butanol, 2-amino-3-methyl-1-propanol, 2-amino-3-pentanol, 3-amino-2-propanol, 2-amino-3-methyl-3-butanol, 2-amino-2-methyl-3-butanol, 1-amino-2-methyl-2-butanol, 2-amino-2-methyl-1-butanol, 1-amino-6-hexanol, 2-amino-6-hexanol, 2-amino-5-hexanol, 1-amino-5-hexanol, 1-amino-4-hexanol, 1-amino-2-hexanol, 2-amino-1-hexanol, 1-amino-2-cyclohexanol, 1-amino-7-heptanol, 1-amino-8-octanol, 1-amino-9-nonanol, 1-amino-10-decanol, 1-amino-11-undecanol, 1-amino-12-dodecanol.

Before conducting process step b), a mixture of the component comprising an azolide moiety in a solvent is typically provided.

According to one embodiment, the solvent is provided first and the urea azolide is added to the solvent.

The component comprising an azolide moiety (e.g. a carbonyl bisazolide) can be dispersed in a solvent. The component comprising an azolide moiety should be at least partially soluble in the solvent.

A solubility of equal or more than about 0.001 wt.-%, equal or more than about 0.01 wt.-% or equal or more than about 0.1 wt.-% of the solid in the solvent can be preferred.

A component can be classified as soluble, if it dissolves in a given solvent at 23° C. and ambient pressure within about 1 h while stirring without leaving any residues visible to the human eye.

In another embodiment the component comprising an azolide moiety (e.g. carbonyl bisazolide) can be added to the pure, dispersed or dissolved amine or ammonium salt as solution, dispersion or as it is, e.g. in pure form.

The inventive process is typically carried out in a solvent. Using a solvent is, however, optional.

The nature and structure of the solvent which may be used is not particularly limited either, as long as the desired reaction product can be obtained.

Solvents which can be used can be characterized by at least one of the following features:
a) Boiling point: In the range of about 30° C. to about 250° C.,
b) Non-reactive or inert with respect to CDI, HCl, acids, basic compounds.
c) Aprotic behaviour (i.e. solvents which cannot donate a proton).
d) Water content: below about 1 wt.-% or below about 0.5 wt.-% or below about 0.1 wt.-% ("dry" solvent).

A combination of the features b) and c) or b) and d) or b), c) and d) is sometimes preferred, especially if a high yield is desired.

It can be preferred, if the boiling point is sufficiently different from the boiling point of the product. This may facilitate the separation e.g. by distillation.

Examples of solvents which can be used include: tetrahydrofuran, toluene, acetonitrile, chloroform, methylene chloride, benzene, heptane, cyclohexane, xylene, methy tert.-butyl ether, ethyl acetate, tetrahydrofurane, methy ethyl ketone, acetone, dioxane, acetonitrile, combinations and mixtures thereof.

Particular solvents which were found not to be generally useful are water, alcohols (e.g. methanol, ethanol, etc.), amines, mixtures and combinations thereof.

The inventive process comprises the process step b) of adding an acid having a pKs below about 4 under exclusion of water or protic solvents at a temperature below about 40° C. This process step is typically conducted in a solvent as well.

The reaction can basically be described as a neutralization reaction between the acid and the azole moiety being present in the urea azolide.

Temperature: If possible, the addition of the acid should be effected at ambient temperature (e.g. about 20 to about 25° C.). As during the neutralization reaction the temperature of the composition typically increases, cooling might be necessary to ensure that the temperature of the reaction composition does not exceed about 40° C. or about 35° C. or about 30° C. or about 25° C.

During the reaction, the composition is typically stirred.

Duration: The acid is typically added over a time period of about 10 min to about 60 min. This, however, typically depends on the reaction volume. For a volume of below about 5 l, the addition can be accomplished within about 20 to 60 min.

Stoechiometry: The acid is typically added in a slight excess with respect to the urea imidazolide. A ratio in the range from about 1:1.01 to about 1:1.5 can be preferred (ratio urea imidazolide/acid).

The nature and structure of the acid which is used for converting the urea azolide into the isocyanate is not particularly limited, either, as long as the desired reaction product can be obtained.

Typically, a strong acid is required (e.g. an acid having a pKs-value below about 4 or below about 2 or below about 1).

The pKs-value can be taken from chemical literature (e.g. "Lange's Handbook of Chemistry", James T. Speight, 16th Ed., McGraw-Hill 2005, Table section 1.69 page 1.330 "Dissociation Constants of Inorganic Acids" and Table Section 2.59 page 2620-2669 "pK, Values of Organic Materials in Water").

The acid can be in solid, liquid or gaseous form.

The acid should preferably be "dry", that is, the water content of the acid should be below about 1 wt.-% or 0.5 wt.-% or 0.2 wt.-%. Water residues may be detrimental in that they may cause a reduced yield of the ultimate product isocyanate.

Acids which can be used include: gaseous acids (like hydrochloric acid (HCl (gas)), sulfonic acids (e.g. toluene sulfonic acid, benzene sulfonic acid, methylsulfonic acid, trifluoromethane sulfonic acid), mixtures and combinations thereof.

It can be beneficial if the acid is able to form an only slightly or essentially insoluble salt with the azoles at the reaction conditions. This may help to push the whole reaction in the direction of the desired isocyanate product.

Conducting process step c) (heating the composition to a temperature above about 70° C.) is optional, but may help to increase the overall yield of the desired product.

It has been observed that during this optional process step, crystallization of the formed azolium salt takes place and that the desired isocyanate product remains in the liquid phase.

Temperature: A typical temperature range for conducting this process step is from above about 70 to about 100° C. or from about 75 to about 95° C. or from about 80 to about 90° C. Typically the temperature should be below the boiling point of the solvent used. Otherwise, further process equipment might be needed.

The temperature can be achieved either by heating the reaction mixture to the desired temperature or by removing the cooling equipment used during process step 1.

Pressure: If present, process step c) may be conducted at ambient pressure (e.g. within a range from about 950 mbar to about 1050 mbar). However, if desired, process step c) can also be conducted at a higher or lower pressure. This typically depends on the volatility or boiling point of the solvent or product.

Duration: If present, process step c) may take place over a time period from a few minutes (e.g. at least about 10, 20 or 30 min) up to a few hours (e.g. at least about 1 or at least about 2 h). This mainly depends on the solvent and acid used and on the amount of reactive components present in the reaction vessel and the solubility of the reactants in the reaction media. A time period of about 10 min to about 10 h was found to be useful.

Conducting process step d) (removing the isocyanate from the reaction mixture) is optional, too.

If desired, removing the isocyanate from the reaction mixture can be conducted by various methods or a combination of various methods. Most of them are known to the person skilled in the art. Those method include decanting the liquid phase, washing the precipitate, drying the combined liquid phases, if desired, evaporating the solvent at reduced pressure, if desired.

These methods are usually conducted, if the isocyanate to be isolated is completely soluble in the solvent used.

If, however, the isocyanate to be isolated is not soluble in the solvent used during process step a), either another more suitable solvent has to be chosen or the isocyanate has to be removed by other means, e.g. by dissolving the precipitate and filtering the reaction mixture, thereby obtaining the insoluble isocyanate as filter cake or residue.

Depending on the structure of the obtained isocyanate further purification steps can be conducted if desired, including distillation or crystallization.

For the particular component 2-Methyl-acrylic acid 2-isocyanato-ethyl ester (MOI), a particular embodiment of the inventive process can be described as follows:

Ethanolamine hydrochloride is acylated with methacroylchloride in toluene. The resulting reaction mixture is typically directly reacted with CDI (preferably at ambient temperature) to give a solution of 2-Methyl-acrylic acid 2-[(imidazole-1-carbonyl)-amino]-ethyl ester suspended with imidazolium hydrochloride. Next, HCl(g) is introduced at approximately about 20 to about 30° C. Eventually, heating to about 80° C. to about 100° C. for about to 0.5 to about 2 h typically completes the reaction to give MOI which can be distilled after removal of precipitates and toluene.

The reaction scheme can be visualized as follows:

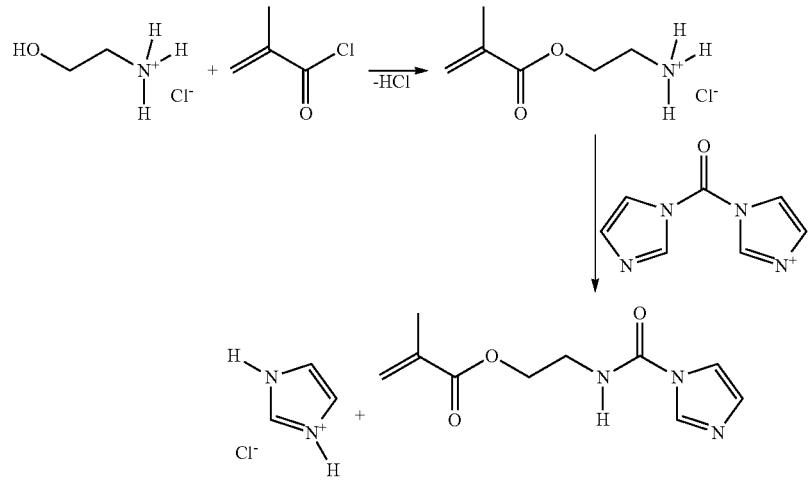

It was found that there is a difference in the final product depending on whether the acid (e.g. HCl(g)) is added to the azolide at low temperature (e.g. ambient temperature or about 30° C.) or at elevated temperatures (e.g. about 70 to about 90° C.).

At low temperatures an increase in viscosity may be observed while the acid (e.g. HCl(g)) is added. The resulting isocyanate (e.g. MOD after heating and distillation is typically essentially pure and typically contains less than about 1000 ppm chloride.

The increase in viscosity may be caused by precipitation of the urea-ammonium salt formed. The addition of acid (e.g. HCl(g)) to the amine function of the urea may destabilize the urea.

Without wishing to be bound to a certain theory, another explanation for the easy cleavage of the urea might be the pre-formation of an imidazolium salt that is more or less incapable of back-reacting with the isocyanate (e.g. MOI).

If, however, HCl is added at elevated temperature, the isocyanate (e.g. MOI) obtained after distillation is typically low in yield and the distillate typically contains a by-product (e.g. presumably a carbamoyl chloride like 2-(2-Methyl-acryloyloxy)-ethyl-carbamoyl chloride) or another chlorine containing compound.

Without wishing to be bound to a certain theory, one explanation might be as follows:

A possible explanation could be that either the salt decomposes or the reactivity at elevated temperatures does not favour the urea salt as product.

The carbamoyl chloride only decomposes well into the isocyanate (e.g. MOI), if a strong tertiary base is present, like triethyl amine. A strong base, however, cannot be used because the reaction of the strong base with the imidazolium chloride by-product is typically faster than the reaction with the covalent carbamoyl chloride.

Releasing imidazole, however, typically leads to backformation of the azolide (e.g. 2-Methyl-acrylic acid 2-[(imidazole-1-carbonyl)-amino]-ethyl ester) from the desired isocyanate (e.g. MOD that has already been formed.

Thus, with respect to this particular example, it was found, that it is possible to produce e.g. MOI from 2-(2-Methyl-acryloyloxy)-ethyl-ammonium; chloride by reacting 2-Methyl-acrylic acid 2-[(imidazole-1-carbonyl)-amino]-ethyl ester with dry hydrogen chloride (HCl(g)) at ambient temperature. The precipitation of imidazolium hydrochloride removes imidazole from the reaction mixture and leaves MOI in solution from which it can be separated.

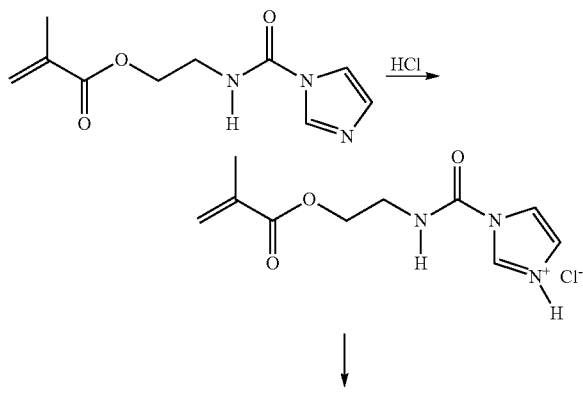

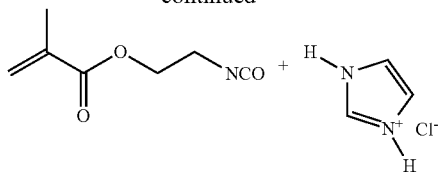

Without wishing to be bound to a particular theory, it is considered that hydrogen chloride primarily forms a chloro-carbamate, which subsequently decomposes to give the desired isocyanate.

It is assumed, that the moderately stable chloro-carbamates are in equilibrium with HCl and the corresponding isocyanate.

Thus, it was found that urea-azolides (including 2-Methyl-acrylic acid 2-[(imidazole-1-carbonyl)-amino]-ethyl ester) can be converted into isocyanates (including MOD with dry HCl gas at temperatures below about 100° C. although the cleavage temperature was expected to be in a range from about 110 to about 130° C.

In addition to that—although typically an excess of HCl is or can be used—the residual chlorine content in the distilled product (i.e. isocyanate) is typically below 1000 ppm.

In another embodiment of the invention, the (e.g. ethylenically unsaturated) isocyanates can be produced according to a process without using a chlorine containing compound.

E.g., (meth)acrylic acid can be esterified with an alkanol amine (e.g. ethanol amine) in the presence of an organic sulphonic acid (including p-toluene sulfonic acid) as described in DE 1929581 A1 (corresponding to U.S. Pat. No. 4,395,569).

This can be beneficial, if the production or use of the expensive and unstable methacroyl chloride is avoided.

The unsaturated sulphonate can be reacted with CDI to obtain an urea imidazolide and the imidazolium salt (e.g. tosylate). The latter can be removed, if desired.

The urea azolide can be treated with an (organic) sulphonic acid (including para toluene sulfonic acid), methane sulfonic acid, benzene sulfonic acid, substituted benzene sulfonic acid, oligofunctional sulfonic acids or alkane sulfonic acids, mixtures and combinations thereof). The treatment is typically done at ambient temperature (e.g. about 20 to about 25° C.). Sulfonic acids with fluorinated substituents or basic substituents (like taurin) are typically not used.

Subsequently the reaction mixture can be heated to produce MOI and the imidazolium salt (e.g. tosylate).

MOI can easily be separated from the mixture. The isolated product (MOI) is virtually free of chlorine. Depending on the residual content of chlorine in the starting material (especially CDI) the chlorine content can be below about 100 ppm, below about 10 ppm or even below about 1 ppm.

If desired, the chlorine content can be analyzed as described in the Example section below.

The isocyanates obtainable by the inventive process can be used broadly in various applications. Those applications include: electronics, printing, medical care (including dental applications and ophthal lenses), automotive, household electric appliances and construction materials. In particular the following use can be envisaged: for producing at least one of the following: solder resist(s), film resist(s), adhesive(s), printing plate(s), soft contact lense(s), dental material(s), coating(s), insulating material(s), cement primer(s) and paint(s) or for surface treatment.

Especially, 2-Methyl-acrylic acid 2-isocyanato-ethyl ester (MOI) is a valuable raw material, which can be used in various fields including the dental and electronic area.

When conducting the inventive process, there is typically no need for the following components to be present, especially no need to willfully add one or more of the following components: strong bases (like tert. amines, including $NEt_3$), phosgene, strong Lewis acids (e.g. $BF_3$, $BCl_3$).

Moreover, the inventive process does typically not contain a process step, where imidazole (as a base) and MOI are separated by distillation.

Various modifications and alterations to this invention will become apparent to those skilled in the art without departing from the scope and spirit of this invention. The above specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope of thereof. The following examples are given to illustrate, but not limit, the scope of this invention. Unless otherwise indicated, all parts and percentages are by weight.

EXAMPLES

Unless otherwise indicated, all parts and percentages are on a weight basis, all water is deionized water, and all molecular weights are weight average molecular weight. Moreover, unless otherwise indicated all Experiments were conducted at ambient conditions (about 23° C.; about 1013 mbar).

The chlorine content can be determined as follows:

About 2 g of the sample to be analyzed were weighed into a round bottle flask. 100 ml of a methanol/water mixture (7:3 by volume) was added. The mixture was heated under reflux to about 75-80° C. for about 1 h. After cooling to room temperature 1 ml of $HNO_3$ (2N) was added. The chlorine content was determined by titration using a 0.0025 N $AgNO_3$/MeOH solution (Titroprozessor). The chlorine content can be calculated as follows:

Cl⁻ (ppm)=(volume of $AgNO_3$/MeOH solution [ml]
*0.0025 [N]*35.45 [g/mol]*100%*10.000
[ppm])/(weight of sample [mg])

ABBREVIATIONS

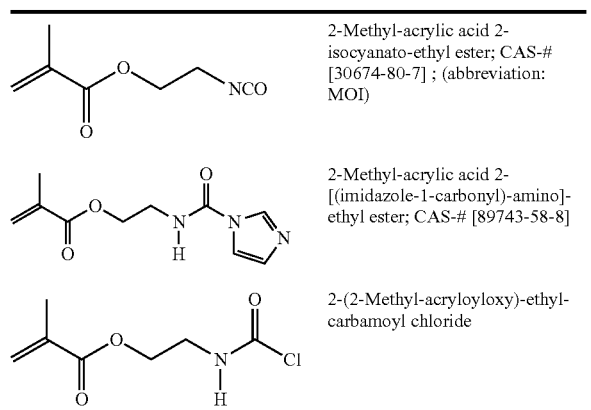

| | 2-Methyl-acrylic acid 2-isocyanato-ethyl ester; CAS-# [30674-80-7] ; (abbreviation: MOI) |
| | 2-Methyl-acrylic acid 2-[(imidazole-1-carbonyl)-amino]-ethyl ester; CAS-# [89743-58-8] |
| | 2-(2-Methyl-acryloyloxy)-ethyl-carbamoyl chloride |

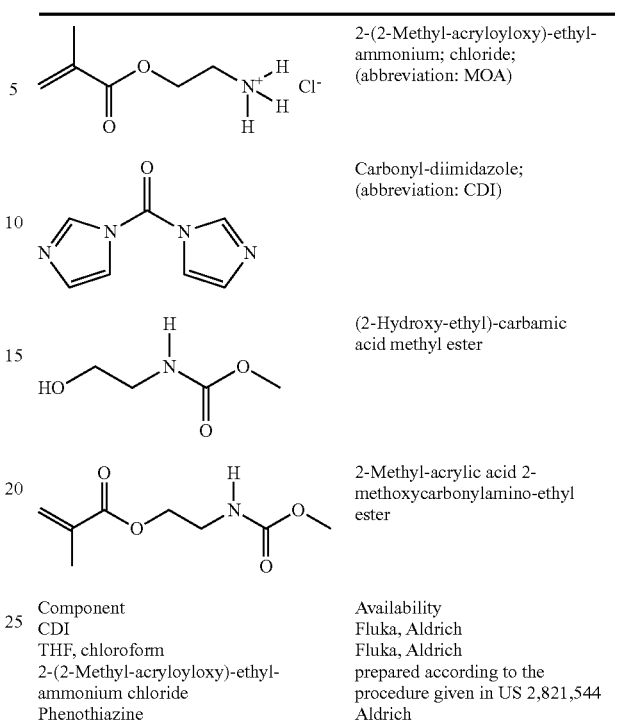

| | 2-(2-Methyl-acryloyloxy)-ethyl-ammonium; chloride; (abbreviation: MOA) |
| | Carbonyl-diimidazole; (abbreviation: CDI) |
| | (2-Hydroxy-ethyl)-carbamic acid methyl ester |
| | 2-Methyl-acrylic acid 2-methoxycarbonylamino-ethyl ester |

| Component | Availability |
|---|---|
| CDI | Fluka, Aldrich |
| THF, chloroform | Fluka, Aldrich |
| 2-(2-Methyl-acryloyloxy)-ethyl-ammonium chloride | prepared according to the procedure given in US 2,821,544 |
| Phenothiazine | Aldrich |

Auxilliary 1

2-(2-Methyl-acryloyloxy)-ethyl-ammonium; chloride (MOA)

Ethanolammonium chloride was reacted with Methacrylic anhydride in Cyclohexane. After separation and purification 122.8 g (62.3% of theory) of the desired product were yielded. The white crystalline solid showed a water content of 0.7% and a chlorine equivalent of 166.5 g/Mole.

Auxilliary 2

2-Isopropylidene-2-oxazoline

Isopropylideneoxazoline was synthesized from 2-(α-hydroxymethylethyl)-2-oxazoline as described in EP 0 000 144 (corresponding to U.S. Pat. No. 4,278,809).

Comparative Example 1

2-Methyl-acrylic acid 2-isocyanato-ethyl ester

2-Methyl-acrylic acid 2-isocyanato-ethyl ester was synthesized as described in EP 0000144. Methacryloxyethylisocyanate (MOI) was produced from 2-Isopropylidene-2-oxazoline and phosgene according to the given procedure and fractionated after separation. The MOI received was 96.3% pure (2.8% toluene). The residual chlorine content found was 2050 ppm.

Example 1

2-Methyl-acrylic acid 2-[(imidazole-1-carbonyl)-amino]-ethyl ester 25.4 g (0.17 mole, >97% FLUKA) CDI were suspended in about 150 ml THF (tetrahydro furane) at room temperature.

Upon partial dissolution the suspension was cooled down to about 17° C. After about 30 min stirring 25.9 g (0.16 mole) 2-(2-Methyl-acryloyloxy)-ethyl-ammonium chloride were added to the mixture under cooling on ice in several portion during about 1 h keeping the reaction mixture at about 23° C. A yellow suspension was obtained. After about 3 h of stirring at about 23° C. the suspension was filtrated. The filter cake was washed with THF. To the clear yellow filtrate about 300 mg phenothiazine were added. Solvent was evaporated. A clear orange viscous resin was obtained (containing traces of residual solvent). Yield was quantitative, $^1$H NMR indicates the desired product.

Example 2

2-Methyl-acrylic acid 2-isocyanato-ethyl ester

In a round bottom flask 35.7 g (156 mmole, 97.8%) 2-Methyl-acrylic acid 2-[(imidazole-1-carbonyl)-amino]-ethyl ester (Example 1) were dissolved in about 100 ml chloroform at room temperature (30 min). The clear yellow solution was diluted with about 100 ml toluene. To the resulting turbid dispersion 11.5 g (313 mmole=200% of theory) dry hydrogen chloride were added at about 23° C. within about 30 min, while cooling. A second liquid phase was formed. The reaction mixture was stirred for another hour. At ambient pressure 123 g of chloroform were distilled from the reaction mixture at about 69-74° C. Thereafter, the vessel was kept at about 91-92° C. for about 1 h. Meanwhile imidazolium hydrochloride began to crystallize giving a greenish suspension. After about 1 hour of stirring at room temperature the toluene phase was decanted, precipitated washed with more toluene. The clear yellow phase was evaporated at about 40° C. and about 25 mbar under exclusion of light. This raw product (according to NMR) consisted of MOI with about 18% residual toluene. It was distilled at about 48° C. and about 1.4 mbar. The clear product was stabilized with 200 ppm phenothiazine. A yield of 52% was obtained with the distilled product. Analytics showed 96.8% purity (GC) and 400 ppm residual chlorine.

Example 3

2-(2-Methyl-acryloyloxy)-ethyl-ammonium; tosylate

In a 500 ml round bottom flask 104.6 g (0.55 Mole) para-toluene sulfonic acid mono hydrate, 43.05 g (0.5 Mole) methacrylic acid, 30.55 g (0.5 Mole) ethanol amine, 150 mg phenothiazine and about 270 ml toluene were mixed. The temperature of the reaction mixture rose to about 70° C. while mixing and the para-toluene sulfonic acid dissolved almost entirely to obtain a clear red two-phase mixture. The reaction mixture was heated to reflux (about 110° C.) at exclusion of light using a Dean-Stark trap. After about 3 h another 150 mg phenothiazine were added. After a sufficient time which can take about 48 h or more 18.5 g (theory 18.9 g) of water was separated. During the time a suspension of finely dispersed solid had built. Toluene was distilled off at about 45° C. The remaining residue was recrystallized. The recrystallized product was filtered and washed with another 250 ml cold ethyl acetate. The white crystalline product was dried at about 45° C. under vacuum to receive 113.1 g (75% of theory). Water content found: 0.15%, melting point 103° C., acid equivalent: 296 g/Mole.

Example 4

2-Methyl-acrylic acid 2-isocyanato-ethyl ester

In a 1000 ml four neck roundbottom flask 35.5 g (200 mMole; 97%) CDI and 22.3 mg phenothiazin were suspended in 200 ml ethyl acetate. The suspension was stirred for about 30 min at about 23° C. The temperature dropped to about 21° C. during that time and CDI dissolved partly. To the stirred suspension 61 g 2-(2-Methyl-acryloyloxy)-ethyl-ammonium; tosylate (200 mMole; 99%) were added in portions within about 30 min such that the temperature of the well agitated reaction mixture did not exceed about 30° C. An off-white to brownish suspension was obtained that was stirred for another about 24 hours. The reaction mixture was filtered and the white precipitate washed with ethyl acetate. The solvent was distilled from the clear yellow to brown filtrate at about 40° C. under exclusion of light. A slightly viscous clear light yellow to brown resin was obtained that, according to proton NMR consisted of 2-Methyl-acrylic acid 2-[(imidazole-1-carbonyl)-amino]-ethyl ester and about 16 wt.-% ethyl acetate. 38.04 g (200 mMole) para-toluene sulfonic acid monohydrate were refluxed together with about 500 ml toluene using a Dean-Stark trap. 3.6 g water (100% theory) had been separated after about 4 h. Thereafter, about 300 ml toluene were distilled off. To this solution a solution consisting of the above synthesized product dissolved in about 50 ml toluene was added within about 30 min such that the temperature of the reaction mixture did not exceed about 30° C. The initially separating yellowish oil crystallized subsequently giving a whitish suspension after about 3 hours of stirring at about 23° C. The suspension was heated to about 80° C. and kept at that temperature for about 3 h. The precipitate disappeared and imidazolium tosylate was formed within about 15 min. The suspension was kept for another about 5 hours at that temperature. The reaction mixture was filtered and the white precipitate washed with about 50 ml toluene. The solvent was removed from the yellow filtrate at about 40° C. at about 50 mbar. Proton NMR indicates that the clear yellow liquid consisted of MOI, toluene and residual uncleaved 2-Methyl-acrylic acid 2-[(imidazole-1-carbonyl)-amino]-ethyl ester. The product was fractionated under vacuum. At about 43° C. and about 1 mbar 20 g product was obtained (64% of theory). The clear colorless liquid had a purity of 98% MOI (GC). The residual chlorine content found was 3 ppm.

Example 5

2-(2-Methyl-acryloyloxy)-ethyl-ammonium; methane sulfonate

This substance was synthesized according to the procedure described in Example 3. Methane sulfonic acid was used as 70% aqueous solution. The product was not re-crystallized. A yield of 84% white crystalline product was obtained. Water content: 0.16%; melting point: 71° C.; acid equivalent: 215 g/Mole.

Example 6

2-Methyl-acrylic acid 2-isocyanato-ethyl ester

This substance was synthesized according to the procedure described in Example 4, second step. 2-Methyl-acrylic acid 2-[(imidazole-1-carbonyl)-amino]-ethyl ester was used from Example 5. Dry methane sulfonic acid was used to protononate and decompose the 2-Methyl-acrylic acid 2-[(imidazole-1-carbonyl)-amino]-ethyl ester. 39.1 g MOI were received after fractionation (62.1% of theory); purity of 97.5%; residual chlorine: not detectable.

Example 7

2-(2-Methyl-acryloyloxy)-ethyl-ammonium; benzene sulfonate

This substance was synthesized according to the procedure described in Example 3. Benzene sulfonic acid was used as 78% aqueous solution. The product was re-crystallized from ethyl acetate. A yield of 85% white crystalline product was obtained. Water content: 0.16%; melting point: 136° C.; acid equivalent: 287 g/Mole.

Example 8

5-(2-Methyl-acryloyloxy)-pentyl-ammonium; tosylate

This substance was synthesized according to the procedure described in Example 3.

104.6 g (0.5 Mole) 5-Amino-1-pentanole were used. The product was re-crystallized from ethyl acetate. A yield of 156 g white crystalline product was obtained (91% of theory); water content: 0.07%; melting point: 127° C.

Example 9

2-Methyl-acrylic acid 5-isocyanato-pentyl ester

In a 1000 ml four neck roundbottom flask about 47.5 g (291 mMole; 97%) CDI and 148 mg phenothiazin were suspended in about 115 ml ethyl acetate. The suspension was stirred for about 30 min at about 23° C. To the stirred suspension 100 g 5-(2-Methyl-acryloyloxy)-pentyl-ammonium; tosylate (291 mMole) were added in portions within about 30 min such that the temperature of the well agitated reaction mixture did not exceed about 30° C. An off-white to brownish suspension was obtained that was stirred for another about 16 h. The reaction mixture was filtered and the white precipitate washed with ethyl acetate. The solvent was distilled from the clear yellow to brown filtrate at about 40° C. under exclusion of light. A slightly viscous clear light brown resin was obtained that, according to proton NMR, consisted of 2-Methyl-acrylic acid 5-[(imidazole-1-carbonyl)-amino]-pentyl ester. 55.4 g (291 mMole) para-toluene sulfonic acid monohydrate were refluxed together with about 250 ml toluene using a Dean-Stark trap. 5.2 g water (100% theory) were separated after about 4 h. To this solution a solution consisting of the above synthesized product dissolved in about 50 ml toluene was added within about 30 min such that the temperature of the reaction mixture did not exceed about 30° C. The initially separating yellowish oil crystallized subsequently giving a whitish suspension after about 3 h of stirring at about 23° C. The suspension was heated to about 80° C. and kept at that temperature for about 3 h. The precipitate disappeared and imidazolium tosylate was formed. The suspension was kept for another 16 h at about 85° C. The reaction mixture was filtered and the white precipitate washed with toluene. The solvent was removed from the yellow filtrate at about 40° C. and at about 50 mbar. Proton NMR indicated that the clear yellow liquid consisted of 2-Methyl-acrylic acid 5-isocyanato-pentyl ester, toluene and residual un-cleaved 2-Methyl-acrylic acid 5-[(imidazole-1-carbonyl)-amino]-pentyl ester. The product was fractionated under vacuum. At about 75° C. and about 0.20 mbar 37.3 g (65% of theory) product was obtained. The clear colorless liquid had a purity of 99.6% MOI (GC). The residual chlorine content found was 75 ppm.

Example 10

2-Methyl-acrylic acid 2-isocyanato-ethyl ester

In a 1000 ml four neck roundbottom flask 163 g (999 mMole) CDI and 476 mg phenothiazin were suspended in about 500 ml toluene. The suspension was stirred for about 30 min at about 23° C. To the stirred suspension 304 g 2-(2-Methyl-acryloyloxy)-ethyl-ammonium; tosylate (999 mMole) were added in portions within about 30 min such that the temperature of the well agitated reaction mixture did not exceed about 30° C. An off-white to brownish suspension was obtained which is stirred for another about 24 h. The reaction mixture was filtered and the white precipitate washed with 500 ml toluene. The solvent was distilled from the clear yellow to brown filtrate at about 40° C. under exclusion of light. A slightly viscous clear light yellow resin was obtained which, according to proton NMR, consisted of 2-Methyl-acrylic acid 2-[(imidazole-1-carbonyl)-amino]-ethyl ester and toluene. 190.22 g (1001 mMole) para-toluene sulfonic acid monohydrate were refluxed together with about 500 ml toluene using a Dean-Stark trap. 18 g water (100% theory) were separated after about 4 h. Thereafter about 300 ml toluene were distilled off. To this solution a solution consisting of the above synthesized product dissolved in about 50 ml toluene was added within about 30 min such that the temperature of the reaction mixture did not exceed about 30° C. The initially separating yellowish oil crystallized subsequently giving a whitish suspension after about 3 h of stirring at about 23° C. The suspension was diluted with about 250 ml toluene. The suspension was heated to about 85° C. and kept at that temperature for about 3 h. The precipitate disappeared and imidazolium tosylate was formed within about 15 min. The suspension was kept for another about 16 h at that temperature. The reaction mixture was filtered and the white precipitate washed with about 500 ml toluene. The solvent was removed from the yellow filtrate at about 40° C. and at about 50 mbar. Proton NMR indicated that the clear yellow liquid consisted of MOI, toluene and residual un-cleaved 2-Methyl-acrylic acid 2-[(imidazole-1-carbonyl)-amino]-ethyl ester. The product was fractionated under vacuum at about 43° C. and about 1 mbar. 81 g was obtained (52.3% of theory). The clear colorless liquid had a purity of 95.1% MOI (Rest: toluene). The residual chlorine content found was 48 ppm.

Example 11

2-Methyl-acrylic acid 2-isocyanato-ethyl ester

The procedure of Example 10 was repeated, but the filter extracted with about 500 ml toluene and the filtrate combined with the mother liquor. After distillation and fractionation 92.6 g (59.7% of theory) MOI was obtained. The clear colorless liquid had a purity of 97% MOI (Rest: toluene; GC). The residual chlorine content found was 47 ppm.

Example 12

2-Methyl-acrylic acid 2-isocyanato-ethyl ester

The procedure of Example 10 was repeated with 2-(2-Methyl-acryloyloxy)-ethyl-ammonium; tosylate prepared according to Example 3 without recrystallization from ethyl acetate but crystallization from the reaction mixture with a sufficient amount of toluene. The first filtration step in the procedure of Example 10 was omitted. The solution of water free-toluene sulfonic acid was added directly to the suspension and procedure continued as described in Example 10. After distillation and fractionation 92.6 g (59.7% of theory) MOI was obtained. The clear colorless liquid had a purity of 99.2% MOI (0.4% toluene; GC). The residual chlorine content found was 16 ppm.

Example 13

Attempted synthesis of 2-Methyl-acrylic acid 2-isocyanato-ethyl ester

A sample of 2.25 g of 2-Methyl-acrylic acid 2-[(imidazole-1-carbonyl)-amino]-ethyl ester prepared according to Example 4 was heated to 210° C. at 0.07 mbar quickly. Few drops of viscous distillate were collected. Distillate crystallized partly and temporarily in the distillation condenser. The distillate was analyzed with 1H-NMR spectroscopy. About 5% 2-Methyl-acrylic acid 2-isocyanato-ethyl ester was present in the distillate the rest was starting material. This shows that although the desired product and imidazole may have formed during the process these components were not easily separable by distillation.

Example 14

3-(2-Methyl-acryloyloxy)-propyl-ammonium; tosylate

In a 6000 ml reactor 837 g (4.4 Mole) para-toluene sulfonic acid mono hydrate, 517 g (6 Mole) methacrylic acid, 300 g (4.0 Mole) 3-amino propanole, 1262 mg phenothiazine and about 1985 g toluene were mixed. The temperature of the reaction mixture rose to about 70° C. while mixing and the para-toluene sulfonic acid dissolved almost entirely to obtain a clear green two-phase mixture. The reaction mixture was heated to reflux (about 110° C.) at exclusion of light using a Dean-Stark trap. After a sufficient time which can take about 48 h or more 152 g of water was separated. During the time a clear orange entirely liquid reaction mixture had formed. Another 331 g toluene was added and the reaction mixture was cooled to room temperature. A crystalline phase formed. The crystallized product was filtered and washed with another 500 ml cold toluene. The off-white product was dried at about 45° C. under vacuum to receive 1191.5 g (94% of theory). Water content found: 0.1%, melting point 121° C., acid equivalent: 315 g/Mole.

Example 15

2-Methyl-acrylic acid 3-isocyanato-propyl ester

In a 1000 ml four neck round bottom flask 67.3 g (412 mMole) CDI and 197.3 mg phenothiazine were suspended in about 500 ml toluene. The suspension was stirred for about 30 min at about 23° C. To the stirred suspension 130 g 3-(2-Methyl-acryloyloxy)-propyl-ammonium; tosylate (412 mMole) were added in portions within about 10 min such that the temperature of the well agitated reaction mixture did not exceed about 40° C. An off-white to brownish suspension was obtained which is stirred for another about 24 h. 78.37 g (412 mMole) para-toluene sulfonic acid monohydrate were refluxed together with about 250 ml toluene using a Dean-Stark trap. 18 g water (100% theory) was separated after about 4 h. Thereafter about 100 ml toluene were distilled off. This solution was added to the suspension at 25° C. within 5 min under cooling such that the temperature of the reaction mixture did not exceed about 45° C. The suspension was diluted with about 100 ml toluene and 500 mg phenothiazine was added. The suspension was heated to about 85° C. and kept at that temperature for about 20 h. The reaction mixture was cooled to room temperature, filtered and the white precipitate washed with about 250 ml toluene. The solvent was removed from the yellow filtrate at about 40° C. at about 50 mbar. Proton NMR indicated that the clear yellow liquid consisted mainly of product and toluene. The product was fractionated under vacuum at about 70° C. and about 0.5 mbar. 52.9 g product was obtained (76% of theory). The clear colorless liquid had a purity of 98.3% 2-Methyl-acrylic acid 3-isocyanato-propyl ester (Rest: toluene; GC). The residual chlorine content found was 23 ppm.

Example 16

3-(Acryloyloxy)-propyl-ammonium; tosylate

In a 1000 ml four neck round bottom flask 105 g (0.55 Mole) para-toluene sulfonic acid mono hydrate, 72 g (1.0 Mole) acrylic acid, 37.56 g (0.5 Mole) 3-amino propanole, 151 mg phenothiazine and about 350 ml toluene were mixed. The temperature of the reaction mixture rose to about 70° C. while mixing and the para-toluene sulfonic acid dissolved almost entirely to obtain a clear green two-phase mixture. The reaction mixture was heated to reflux (about 110° C.) at exclusion of light using a Dean-Stark trap and another 151 mg phenothiazine was added. After a sufficient time which can take about 48 h or more 19 g of water was separated. During the time a suspension clear orange entirely liquid reaction mixture had formed. The reaction mixture was cooled to room temperature. A crystalline phase formed. The crystallized product was filtered and washed with another 200 ml cold toluene. The white product was dried at about 45° C. under vacuum to receive 146 g (97% of theory). Water content found: 0.1%, melting point 106° C., acid equivalent: 287 g/Mole. The product can be converted into Acrylic acid 3-isocyanato-propyl ester by a procedure similar to Example 15.

The invention claimed is:
1. A process for producing isocyanates comprising the steps of
a) providing a component with an azolide moiety and optionally a solvent,
b) adding an acid at a temperature below about 40° C.,
c) optionally heating the composition to a temperature above about 70° C. and
d) optionally removing or isolating the isocyanate from the reaction mixture;
wherein the acid has a pKa-value below about 2,
wherein the process is conducted under non-aqueous conditions, and
wherein the isocyanate is characterized by the following structure:

G-K—NCO          (1)

with G comprising an acyloyl moiety and
K being a $C_2$ to $C_{12}$ saturated or unsaturated linear, branched, cyclic alkylidene or aromatic residue or a combination thereof, wherein hydrogen might be replaced by halogen and wherein the carbon chain can be interrupted by one, two, three or four oxygen atoms.
2. The process according to claim 1, wherein process step b) is characterized by at least one or more of the following features:
Temperature: within a range of about 10 to below about 40° C., Amount of acid: at least stoichiometric with respect to the component with an azolide moiety,
Duration: addition of acid within about 1 h.

3. The process according to claim 1, wherein process step c) is characterized by at least one or more of the following features:
Temperature: within a range of about 70 to about 100° C.,
Duration: about 1 min to about 10 h.

4. The process according to claim 1, wherein process step d) comprises one or more of the following procedures: decanting, washing, drying, evaporating, distillation, crystallization or combinations thereof.

5. The process according to claim 1, characterized by at least one or more of the following features:
no use of phosgene,
chloride content of isolated isocyanate: below about 1000 ppm.

6. The process according to claim 1, wherein the component with the azolide moiety is obtained
either by reacting an amine with an azole containing compound according to the following structure

with A comprising an azole ring connected to the carbonyl group via an N atom or
where an amine compound is reacted in a first step with phosgene and in a second step with an azole under formation of an azolide.

7. The process according to claim 1, wherein the component comprising the azolide moiety is obtained by reacting an azole containing compound with an amine, its corresponding ammonium salt or mixtures thereof, the amine being characterized by the following structure:

with G comprising an acyloyl moiety and K being a $C_2$ to $C_{12}$ saturated or unsaturated linear, branched, cyclic alkylidene or aromatic residue or a combination thereof, wherein hydrogen might be replaced by halogen and wherein the carbon chain can be interrupted by one, two three or four oxygen atoms or ester moieties.

8. The process according to claim 6, wherein the azole containing compound is selected from 1,1'-carbonyl-diimidazol, 1,1'-carbonyl-dibenzimidazol, 1,1'-carbonyl-di-(1,2,4)-triazol, 1,1'-carbonyl-bis-(2-methylimidazol), 1,1'-carbonyl-dibenzotriazol, combinations and mixtures thereof.

9. The process according to claim 1, wherein the acid is selected such that it can form a salt with imidazole which is only insoluble in the optionally used solvent.

10. The process according to claim 1, wherein the acid is selected from the group consisting of gaseous acids, sulfonic acid, mixtures and combinations thereof.

11. The process according to claim 1, wherein the optionally used solvent is selected from the group consisting of tetrahydrofuran, toluene, acetonitrile, chloroform, methylene chloride, benzene, heptane, cyclohexane, xylene, methy tert.-butyl ether, ethyl acetate, tetrahydrofurane, methy ethyl ketone, acetone, dioxane, acetonitrile, combinations and mixtures thereof.

12. The process according to claim 1, wherein the isocyanate is selected from the group of acrylic acid 2-isocyanato-ethyl ester, 2-Methyl-acrylic acid 2-isocyanato-ethyl ester, acrylic acid 2-isocyanato-propyl ester, 2-Methyl-acrylic acid 2-isocyanato-propyl ester, acrylic acid 3-isocyanato-propyl ester, 2-Methyl-acrylic acid 3-isocyanato-propyl ester, acrylic acid 4-isocyanato-butyl ester, 2-Methyl-acrylic acid 4-isocyanato-butyl ester, acrylic acid 5-isocyanato-pentyl ester, 2-Methyl-acrylic acid 5-isocyanato-pentyl ester, acrylic acid 6-isocyanato-hexyl ester, 2-Methyl-acrylic acid 6-isocyanato-hexyl ester, acrylic acid 8-isocyanato-octyl ester, 2-Methyl-acrylic acid 8-isocyanato-octyl ester, acrylic acid 10-isocyanato-decyl ester, 2-Methyl-acrylic acid 10-isocyanato-decyl ester, acrylic acid 11-isocyanato-undecyl ester, 2-Methyl-acrylic acid 11-isocyanato-undecyl ester, acrylic acid 12-isocyanato-dodecyl ester, 2-Methyl-acrylic acid 12-isocyanato-dodecyl ester, acrylic acid 1-(2,3-diisocyanato-propyl)ester, 2-Methyl-acrylic acid 1-(2,3-diisocyanato-propyl)ester, acrylic acid 2-(1,3-diisocyanato-propyl) ester, 2-Methyl-acrylic acid 2-(1,3-diisocyanato-propyl)ester, acrylic acid 1,2-(3-isocyanato-propyl)diester, 2-Methyl-acrylic acid 1,2-(3-isocyanato-propyl)diester, acrylic acid 1,3-(2-isocyanato-propyl)diester, 2-Methyl-acrylic acid 1,3-(2-isocyanato-propyl)diester.

* * * * *